United States Patent [19]

Golay

[11] Patent Number: 4,856,319

[45] Date of Patent: Aug. 15, 1989

[54] THERMALLY SWITCHABLE KATHAROMETER

[75] Inventor: Marcel E. Golay, La Conversion, Switzerland

[73] Assignee: The Perkin-Elmer Corporation, Norwalk, Conn.

[21] Appl. No.: 200,335

[22] Filed: May 31, 1988

[51] Int. Cl.$^4$ .............................................. G01N 31/08
[52] U.S. Cl. ........................................ 73/23.1; 422/89
[58] Field of Search ................... 73/27 R, 25, 23.1; 422/89, 90; 436/161

[56] References Cited

U.S. PATENT DOCUMENTS 4,464,925 8/1984 Koloff .................................... 73/23.1

*Primary Examiner*—Hezron E. Williams
*Attorney, Agent, or Firm*—Ronald G. Cummings; Edwin T. Grimes; Thomas P. Murphy

[57] ABSTRACT

A gas chromatography system having a chromatography column, a detector for analyzing sample components with a detection chamber connected to the column outlet, and a switching assembly for selectively alternately filling the detector chamber with carrier gas for a base line measurement and with effluent for analysis. The switching assembly includes a gas chamber connected to the detector chamber, a source of carrier gas and hot wire filament for selectively heating gas in the gas chamber to cause the carrier to be expelled from the gas chamber to fill the detection chamber for a base line measurement and for cooling gas in the gas chamber to withdraw the carrier gas from the detection chamber so as to draw effluent from the column outlet to thereby fill the detection chamber for an analytical measurement.

12 Claims, 1 Drawing Sheet

THERMALLY SWITCHABLE KATHAROMETER

BACKGROUND AN SUMMARY OF THE INVENTION

This invention relates generally to the introduction of eluted sample components into a gas chromatography detector and more particularly to an apparatus and technique for switching between the introduction of pure carrier gas and sample components in a kathorometer.

Generally, in gas chromatography, the sample to be analyzed is introduced into the chromatography column in a stream of carrier gas. The separation process takes place in the column and at the end of the column the individual components will emerge more or less separated in time. The individual components separated by the column are detected by continuously monitoring some physical or chemical properties of the effluent.

Ideally, each component in the sample emerges from the column at different times so that, at any one time, the gas flowing into the detector is either all carrier gas or a combination of carrier gas and one of the components of the sample. The detector functions by producing a signal related to the change in the intensity of a given characteristic of the gases flowing through it. As each sample component passes through the detector, the output signal varies from the value it has when the detector is full of carrier gas, with the amount of variation depending on the concentration of the sample component.

A widely used detector is the thermal conductivity detector (also referred to as a hot wire detector or katharometer) which measures the differences in the thermal conductivity of the pure carrier gas and the mixture of the sample component and the carrier gas. Other types of detectors include the flame ionization detector, the electron capture detector, the thermionic detector and the flame photometric detector.

A typical thermal conductivity detector includes a block having a cavity therein with a filament suspended in the cavity and ports at either end of the filament. One of the ports is connected to the outlet end of the chromatogrphy column. Current is passed through the filament so as to heat it and means are generally provided for maintaining the block and therefore the walls of the cavity at a fixed temperature that is less than the temperature of the filament. The output signal of the detector corresponds to the variation in voltage applied to the filament or the current flowing through it that are required to keep the filament at a given temperature or resistance. The temperature of the filament depends on the rate at which heat can flow from it to the walls of the cavity. Nearly all the heat flows by conduction through the gases between the filament and the walls of the cavity. Generally, helium is used as a carrier gas because of its inertness and the fact that its thermal conductivity is greater than that of all gasses except hydrogen.

In operation, the flow of gas through the detector is switched between pure carrier gas (for reference measurements) and effluent from the column. Such switching may be accomplished by mechanical switching arrangements such as the rotary valve configuration disclosed in Kolloff, U.S. Pat. No. 4,464,925 for HYDROGEN, DETERIUM THERMALCONDUCTIVITY DETECTOR issued Aug. 4, 1984 and incorporated herein by reference. This configuration utilizes a motor and rotary valve to accomplish the desired switching.

It is an object of the present invention to provide a new and improved gas chromatography system.

Another object of the invention is to provide a new and improved apparatus and technique for alternately filling the detector of such a system with carrier gas and column effluent.

A further object of the invention is to provide such an apparatus for rapidly switching between carrier gas and effluent which does not utilize moving parts.

Another object is to provide such an apparatus which is economical, reliable and efficient.

Other objects will be in part obvious and in part pointed out more in detail hereinafter.

Accordingly, it has been found that the foregoing and related objects and advantages can be obtained in a gas chromatography system having a chromatography column and a detector with a detector chamber connected to the column outlet. A switching assembly for selectively, alternately filling the detector chamber with carrier gas for a baseline measurement and with effluent for analysis is connected to the detector and includes a gas chamber connected to the detector chamber, a source of carrier gas connected to the gas chamber, and apparatus for selectively heating gas in the gas chamber to cause carrier gas to be expelled from the gas chamber to fill the detection chamber for a baseline measurement and for cooling gas in the gas chamber to withdraw the carrier gas from the detection chamber so as to draw effluent from the column outlet to thereby fill the detection chamber for an analytical measurement. The heating apparatus includes a hot wire filament mounted in the gas chamber and electrically controlled for selective heating.

DESCRIPTION OF THE PREFERRED EMBODIMENT

Figure 1:
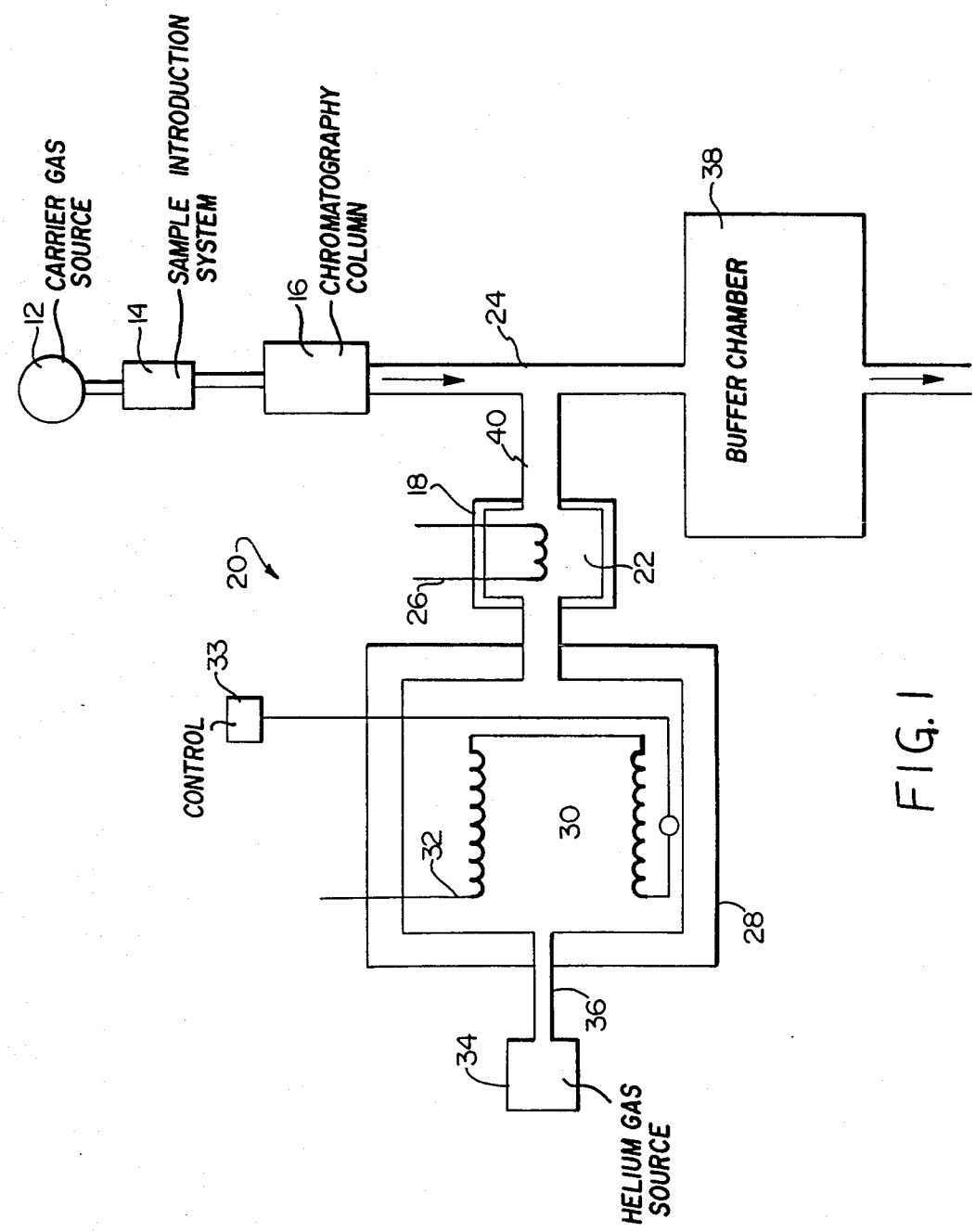
FIG. 1 is schematic diagram of a gas chromatography system of the present invention.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the gas chromatography system of the present invention generally comprises a source of carrier gas 12, a sample introduction system 14, a chromatography column 16, a thermal conductivity detector 18, and a switching assembly generally designated by the numeral 20.

The sample introduction system 14 and column 16 are conventional and need not be described in detail for purposes of the present invention. The thermal conductivity detector 18 is also generally of conventional design having an interior detection chamber 22 fluidly connected by a connector 40 to the outlet 24 of column 16 to recieve effluent therefrom. A hot wire filament 26 is mounted within the chamber 22 and is connected to a control means (not shown) for supplying current to the filament to heat it and measure the variation in voltage or current therein as an output signal. The volume of the detection chamber 22 is relatively small being typically two microliters.

The switching assembly 20 comprises a switching cell 28 forming an interior gas chamber 30. The cell chamber 30 is fluidly connected to the detection chamber 22 and is relatively larger being typically 100 microliters. A hot wire or heating element 32 is mounted within chamber 30 and is connected to an electric control 33 for controlling current flow to selectively heat gas in the cell chamber 30 so as to expel the gas into the detection chamber 22. A source of helium gas 34 is connected to the cell chamber 30 by a pneumatic resistance connector 36 to provide a controlled minute flow of helium into the cell chamber 30.

The switching cell 28, cell chamber 30, hot wire 32, and detection chamber 22 are relatively configured and appropriately dimensioned such that activation of the hot wire 32 heats the helium in cell chamber 30 so as to expell it into detection chamber 22 and fill chamber 22 with pure helium. The helium displaces the gas in detector chamber 22 expelling it through the connector 40 into the main chromatography gas stream indicated by the flow arrows in FIG. 1. The walls of cell 28 are configured and maintained by conventional means at a predetermined temperature sufficiently cool so as to be able to quickly cool the heated gas in cell chamber 30 upon deactivation of hot wire 32 to effect the withdrawal of gas from detection chamber 22 into cell chamber 30. Accordingly, upon deactivation of the hot wire 32, the cooler walls of the cell 28 quickly cool the heated gas in cell chamber 30 thereby causing the volume of pure helium in detection chamber 22 to be withdrawn into cell chamber 30 and causing effluent from the column 16 to be drawn into the detection chamber 22 for measurement. In effect, a controlled pumping action is attained without the necessity of moving parts.

The gas source 34 functions to deliver a minute gas flow through cell chamber 30 sufficient to replace the volume of detection chamber 22 after a predetermined number of measurement operations as described hereinafter. The small helium gas flow serves to maintain the cell chamber 30 free of contaminants which could vitiate the measurements of the detector 18. A relatively large buffer chamber 38 is connected to the outlet 24 of column 16 to isolate the chambers 22, 30 from atmospheric pressure fluctuations.

In operation, the hot wire 32 is activated to heat the helium in cell chamber 30 to fill the detection chamber 22 with pure helium expelled from the cell chamber 30. The thermal conductivity of the pure helium is measured for approximately 10 milliseconds to provide a baseline. The control 33 deactivates the hot wire 32 allowing the gas in chamber 30 to quickly cool and cause the withdrawal of the volume of gas from chamber 22 into chamber 30 to thereby draw sample into the detection chamber 22. The thermal conductivity of this sample is measured for approximately 90 milliseconds and the cycle is then repeated. Consequently, the baseline and the sample measurement operation is repeated approximately 10 times per second. Buffer intervals after each of the switching operations, e.g., 1 millisecond, may be utilized to insure that all measurements are taken in a condition of sufficient quiescence. Pneumatic and thermal time constants are calculated on the order of approximately 1 millisecond. The switching cell 20 is accordingly dimensioned and configured relative to the detector 18 to attain such operation and may be varied as desired to accommodate particular system applications. Other acceptable means of heating and cooling the gas in cell chamber 30 may be substituted.

The flow of helium from source 34 is regulated to deliver to cell chamber 30 a gas flow sufficient to replace the volume of detection chamber 22 after ten sequential measurement operations in order to maintain the gas in cell chamber 30 free of sample contaminants that would adversely effect the accuracy of the measurements obtained.

As can be seen, a new and improved apparatus and technique is provided for alternately and periodically charging the detector of a gas chromatography system with carrier gas for baseline measurements and column effluent for sample measurements. The rapid switching or pumping of carrier gas and effluent is attained by an electrically controlled apparatus which does not utilize moving parts and is accordingly economical, reliable and efficient.

As will be apparent to persons skilled in the art, various modifications and adaptations of the structure above described will become readily apparent without departure from the spirit and scope of the invention, the scope of which is defined in the appended claims.

I claim:

1. A gas chromatography system comprising
    a gas chromatography column having an inlet and outlet,
    detector means for analyzing sample components, said detector means having a detection chamber connected to the column outlet, and
    means for selectively alternately filling said detection chamber with carrier gas for a baseline measurement and with effluent from said column outlet for a sample measurement,
    said means for selectively alternately filling said detection chamber comprising
    a gas chamber connected to said detection chamber,
    means for supplying carrier gas to said gas chamber, and
    means for selectively heating gas in said gas chamber to cause carrier gas from said gas chamber to fill said detection chamber and thereafter cooling gas in said gas chamber to withdraw gas in said detector chamber into said gas chamber so as to draw effluent from said column outlet to fill said detection chamber for a sample measurement.

2. The system of claim 1 wherein said means for filling said detection chamber comprises a cell body having walls forming said gas chamber and hot wire heating means mounted within said cell body for selectively heating gas in said gas chamber to expel carrier gas from said gas chamber to fill said detection chamber.

3. The system of claim 2 wherein said hot wire heating means is mounted within said gas chamber and said walls of said cell body are dimensioned and configured relative to said gas chamber so as to be able to maintain a predetermined temperature sufficient to cool heated gas within said gas chamber upon deactivation of said hot wire heating means to withdraw the gas in said detector chamber into said gas chamber and thus cause effluent from said column outlet to be drawn into said detection chamber.

4. The system of claim 3 comprising means for controlling said hot wire heating means for periodically alternately filling said detection chamber with carrier gas and column effluent.

5. The system of claim 1 comprising control means for periodically, alternately heating gas in said gas chamber to cause carrier gas from said gas chamber to fill said detection chamber for a baseline measurement and cooling gas in said gas chamber to withdraw gas from said detector chamber into said gas chamber to draw column effluent to fill said detection chamber for a sample measurement.

6. The system of claim 1 comprising a buffer chamber means connected to said column outlet for isolating said detection chamber and said gas chamber from atmospheric pressure fluctuations.

7. The system of claim 1 wherein said means for supplying carrier gas comprises a source of carrier gas and connector means connecting said source and said gas chamber for controlling the flow rate of carrier gas into said gas chamber.

8. A method of alternately pumping effluent and carrier gas into a detection chamber in fluid communication with an effluent flow stream comprising the steps of providing a gas chamber of carrier gas in fluid communication with said detection chamber, heating the carrier gas in said gas chamber sufficiently to expel carrier gas into said detection chamber to fill said detection chamber with carrier gas, and thereafter cooling the carrier gas in said chamber sufficiently to withdraw gas from said detection chamber into said gas chamber so as to cause effluent to be drawn into said detection chamber.

9. The method of claim 8 comprising alternately, periodically repeating the steps of heating the carrier gas in said gas chamber and thereafter cooling this carrier gas, performing a first detection measurement whenever said detector chamber is filled with carrier gas, and performing a second detection measurement whenever said detector chamber is filled with effluent.

10. The method of claim 8 wherein the step of heating the carrier gas comprises electrically heating the carrier gas.

11. The method of claim 10 wherein the step of cooling the carrier gas comprises conductively cooling the carrier gas.

12. The method of claim 8 wherein the step of cooling the carrier gas comprises conductively cooling the carrier gas.

* * * * *